(12) United States Patent
Bartkoski et al.

(10) Patent No.: US 10,870,018 B2
(45) Date of Patent: Dec. 22, 2020

(54) APPARATUS AND METHODS FOR MAGNETIC CONTROL OF RADIATION ELECTRON BEAM

(71) Applicants: Board of Regents, The University of Texas System, Austin, TX (US); TEL-HASHOMER MEDICAL RESEARCH INFRASTRUCTURE AND SERVICES LTD. AT THE CHAIM SHEBA MEDICAL CENTER, Ramat-Gan (IL)

(72) Inventors: Dirk Bartkoski, Houston, TX (US); Dror Alezra, Rishon Lezion (IL); Mohammad Salehpour, Houston, TX (US); Thomas Buchholz, Houston, TX (US)

(73) Assignees: Board of Regents, The University of Texas System, Austin, TX (US); Tel-Hashomer Medical Research Infrastructure and Services Ltd. at the Chaim Sheba Medical Center, Ramat-Gan (IL)

( * ) Notice: Subject to any disclaimer, the term of this patent is extended or adjusted under 35 U.S.C. 154(b) by 102 days.

(21) Appl. No.: 16/331,459

(22) PCT Filed: Sep. 5, 2017

(86) PCT No.: PCT/US2017/050066
§ 371 (c)(1),
(2) Date: Mar. 7, 2019

(87) PCT Pub. No.: WO2018/048796
PCT Pub. Date: Mar. 15, 2018

(65) Prior Publication Data
US 2019/0217125 A1    Jul. 18, 2019

Related U.S. Application Data

(60) Provisional application No. 62/385,346, filed on Sep. 9, 2016.

(51) Int. Cl.
*A61N 5/10* (2006.01)
*G21K 1/093* (2006.01)

(52) U.S. Cl.
CPC .......... *A61N 5/1043* (2013.01); *G21K 1/093* (2013.01); *A61N 2005/1089* (2013.01)

(58) Field of Classification Search
USPC .......................... 250/396 ML, 396 R, 492.3
See application file for complete search history.

(56) References Cited

U.S. PATENT DOCUMENTS 3,155,860 A   11/1964  Goetze
3,903,421 A   9/1975   Benedetti
(Continued)

FOREIGN PATENT DOCUMENTS

KR      10-1416559       7/2014
WO      WO 2016/044536   3/1916
(Continued)

OTHER PUBLICATIONS

Extended European Search Report issued in European Application No. 17849392.0, dated Mar. 13, 2020.
(Continued)

*Primary Examiner* — Kiet T Nguyen
(74) *Attorney, Agent, or Firm* — Parker Highlander PLLC (57) ABSTRACT

Apparatus and methods for controlling a radiotherapy electron beam. Exemplary embodiments provide for focusing the electron beam at different depths by altering parameters of a plurality of magnets. Exemplary embodiments can also
(Continued)

provide for focusing the electron beam at different depths while maintaining the energy level of the electron beam at a consistent level.

20 Claims, 9 Drawing Sheets (56) References Cited

U.S. PATENT DOCUMENTS

| | | | |
|---|---|---|---|
| 4,726,046 | A † | 2/1988 | Nunan |
| 4,806,766 | A | 2/1989 | Chisholm |
| 5,113,162 | A | 5/1992 | Umehara et al. |
| 5,161,546 | A | 11/1992 | Bronn |
| 6,292,538 | B1 | 9/2001 | Hell et al. |
| 8,350,226 | B2 | 1/2013 | Zdasiuk et al. |
| 8,436,326 | B2 | 5/2013 | Glavish et al. |
| 8,933,651 | B2 | 1/2015 | Balakin et al. |
| 9,095,705 | B2 | 8/2015 | Trbojevic |
| 9,153,409 | B2 | 10/2015 | Wiedmann et al. |
| 9,283,407 | B2 | 3/2016 | Benna et al. |
| 9,289,624 | B2 | 3/2016 | Jongen |
| 2006/0178577 | A1 | 8/2006 | Iwanczyk et al. |
| 2010/0256791 | A1 | 10/2010 | Spicer et al. |
| 2011/0180731 | A1 | 7/2011 | Welsh |
| 2011/0210263 | A1 | 9/2011 | Abs et al. |
| 2013/0259198 | A1 | 10/2013 | Alezra et al. |
| 2015/0187538 | A1 | 7/2015 | Canfield et al. |
| 2016/0193482 | A1* | 7/2016 | Fahrig ............ A61N 5/1064 600/1 |
| 2018/0154183 | A1* | 6/2018 | Sahadevan ...... A61M 1/3496 |

FOREIGN PATENT DOCUMENTS

| | | |
|---|---|---|
| WO | WO 2012/070054 | 5/2012 |
| WO | WO 2015/102680 | 7/2015 |

OTHER PUBLICATIONS

Böhlen et al., "The FLUKA code: developments and challenges for high energy and medical applications," *Nuclear Data Sheets*, 120:211-214, 2014.

Ferrari et al., "FLUKA: a multi-particle transport code," CERN European Organization for Nuclear Research, 2005.

Lim et al., "Adjustable, short focal length permanent-magnet quadrupole based electron beam final focus system" *Review of Modern Physics*, 8(7):072401, 2005.

Nakajima et al., "Laser-driven very high energy electron/proton beam radiation therapy in conjunction with a robotic system," *Appl. Sci.*, 5:1-20, 2015.

PCT International Search Report and Written Opinion issued in International Application No. PCT/US2017/050066, dated Nov. 13, 2017.

Y. Glinecm, et al., Radiotherapy with laser-plasma accelerators: Monte Carlo simulation of dose deposited by an experimental / quasimonoenergetic electron beam, 9 pages, Dec. 27, 2005, US.†

Ingo Hofmann, Performance of solenoids vs. quadrupoles in focusing and energy selection of laser accelerated protons, 7 pages, Jan. 29, 2013.†

Stefan Lorin, et al., Development of a compact proton scanning system in Uppsala with a moveable second magnet, 13 pages, May 2000.†

O. Lundh, et al., Comparison of measured with calculated dose distribution from a 120-MeV electron beam from a laser-plasma accelerator, 8 pages, May 29, 2012.†

Tim Waldron, Handout for "The Theory and Operation of Computer-Controlled Medical linear Accelerators" MO-A-517A-01, 19 pages, Jul. 15, 2002.†

\* cited by examiner
† cited by third party

APPARATUS AND METHODS FOR MAGNETIC CONTROL OF RADIATION ELECTRON BEAM

CROSS-REFERENCE TO RELATED APPLICATIONS

This application is a national phase application under 35 U.S.C. § 371 of International Application No. PCT/US2017/050066, filed Sep. 5, 2017, which claims priority to U.S. Provisional Patent Application Ser. No. 62/385,346 filed Sep. 9, 2016 and entitled "APPARATUS AND METHODS FOR MAGNETIC CONTROL OF RADIATION ELECTRON BEAM", the entire contents of each of which are incorporated herein by reference.

BACKGROUND INFORMATION

Electron beam radiation therapy utilizes ionizing radiation, typically as part of cancer treatment to destroy malignant cells. Radiation therapy may be curative in a number of types of cancer if they are localized to one area of the body. It may also be used as part of adjuvant therapy to prevent tumor recurrence after surgery to remove a primary malignant tumor. For example, electron beam radiation therapy may be used as part of adjuvant therapy in the early stages of certain types of cancer such as breast cancer.

Radiation therapy is commonly applied to the cancerous tumor due to its ability to control cell growth. Ionizing radiation works by damaging the DNA of cancerous tissue leading to cellular death. To reduce exposure of healthy tissues (e.g. tissues which radiation must pass through to treat the tumor), radiation beams can be aimed from different angles to intersect at the tumor.

Electron beam radiation therapy is currently used to direct radiation to a target region (e.g. a region containing the tumor) to destroy cells within the target region. Typical electron systems are limited in the depth that a target region can be successfully treated. In addition, typical systems do not provide dynamic control of the radiation depth and can direct unwanted radiation to healthy tissues surrounding the target region.

For example, with existing systems the beam energy is manually selected to control the depth of radiation penetration up to a peak dose depth of approximately 3 cm (determined by currently commercially available maximum clinical electron beams energy of 20 MeV). In such systems the beam energy is increased in order to increase the depth of radiation penetration. This provides for higher radiation levels for tissue at or near the surface, and can lead to unwanted excessive radiation exposure to surrounding healthy tissue.

Accordingly, a need exists for new radiation therapy apparatus and methods that provide greater control of radiation dosage levels at varying depths and minimize radiation exposure to surrounding healthy tissues.

SUMMARY

As explained in more detail below, exemplary embodiments of the present disclosure enable improvements in many aspects of electron beam radiation therapy as compared to current apparatus and methods.

Exemplary embodiments of the present disclosure include an electron beam delivery and control system using very high energy electrons (VHEE) to produce a localized focal spot of high radiation dosage within the target volume. Exemplary embodiments are able to control the location of the focal spot through a technique referred to herein as magnetically optimized very high energy electron treatment (MOVHEET).

Apparatus incorporating MOVHEET techniques can be dynamically controlled to produce a distribution of radiation dosage within a target region (e.g. a tumor volume) that is higher than surrounding normal tissue. This ability can result in greater normal tissue sparing and a larger degree of radiation control around the tumor volume. Exemplary embodiments include the ability to dynamically focus an electron beam of 50-250 megaelectron volts (MeV) to a focal spot at a desired target depth. As used herein, the term "depth" when used in reference to the focal spot refers to a dimension measured parallel to the electron beam (e.g. parallel to the primary axis of the beam prior to entering the magnetic control apparatus). The desired target depth can be determined by a radiation treatment plan dose distribution, where the output of the focusing system is a beam with optimized symmetry and a focusing angle that results in a low beam density at the target surface producing low entrance dose.

Methods for dynamically controlling the focal spot depth of the electron focusing system can include the use of magnetic fields outside the target volume to alter the electron trajectories to produce the desired beam behavior.

One embodiment of the focusing system utilizes quadrupole magnetic fields which are produced by a magnet having four inwardly directed poles such that each adjacent pole carries a magnetic field of opposite polarity. Current-carrying coils can be arranged in such a way to produce a magnetic field inside the ferromagnetic magnet material, where the strength of the magnetic quadrupole field may be adjusted by varying the coil current. This type of magnet design is referred to as iron-dominated.

Another embodiment of a quadrupole magnet is based on a coil-dominated design where the current-carrying coils are designed in such a way such that the magnetic multipole field experienced by the charged particle beam is produced directly by the coils themselves without the use of a ferromagnetic core. Varying the current in the coils adjust strength of the magnetic field.

A quadrupole magnetic field has the effect of defocusing a charged particle beam in one plane while focusing the beam in the orthogonal plane. This can allow for overall focusing in both planes being accomplished with a combination of quadrupole magnets whose currents, positions, and other magnet parameters have been chosen to produce the desired beam. A variety of exit beam shapes may be used, and certain configurations of quadrupoles may be used to generate symmetric beams.

In one such configuration, a combination of three collinear quadrupole magnets can produce symmetrically focused beams for parallel incoming electron beams. Such systems can also provide for stigmatic focusing of a diverging beam where the beam focal spot may be adjusted by varying the quadrupole magnet strengths (alone or in conjunction with other parameter alterations).

In another such configuration, a combination of two collinear quadrupole magnets can be use to produce output beams with an oblong shape that may be ideal for certain dose distributions that have strict spatial tolerances due to surrounding critical structures. The use of quadrupole systems with two or three quadrupoles allows for the user to choose the appropriate focusing distribution based on the target area.

For example, in order to attain the desired depth dose distribution for the range of depths typically used for clinical treatment (e.g. 0-35 centimeters), the quadrupole separation distances and triplet position can be varied to achieve the optimal treatment beam. During operation, a quadrupole magnet system can produce a focused beam when the quadrupoles are operated under a specific set of conditions determined by the solution to a system of differential equations that govern the trajectories of the electrons within the field regions.

In exemplary embodiments, a control system for the magnet parameters takes the dose distribution from the treatment planning software and uses an algorithm to calculate the necessary focusing system parameters to produce the desired beam trajectories.

The beam can also be scanned laterally by means of orthogonal dipole fields which produce a uniform offset to the beam in their respective directions to produce a three-dimensional dose distribution. Other embodiments may mechanically move the focusing system to produce a three-dimensional dose distribution. The lateral scanning parameters can be included in the beam control system and determined by the treatment planning software.

For focusing systems using diverging input beams, the beam divergence and origination point are also variables that can be determined by the control system algorithm. As an example, a pencil beam may be made divergent by the use of a scattering foil designed to produce a unique divergence pattern, where the divergent beam is then passed through a collimator in order to restrict the divergence angle for input into the quadrupole focusing system. The relative locations between the scattering foil, collimator, and quadrupole entrance are unique for a particular exit beam and can be determined along with the quadrupole settings.

It should be noted that magnetic fields can have inherent inconsistencies or errors that can translate into nonuniformities in the focused electron beam. Careful consideration for such inconsistencies may be taken into account with the use of sextupole and octupole configurations, for example, to compensate for various geometrical and chromatic inconsistencies. One embodiment of the focusing system may use a quadruplet of quadrupole magnets coincident with three interspersed octupole magnets to produce a focused beam with geometrical aberration correction.

In certain embodiments, an algorithm may be used to solve for the magnet parameters that produce a symmetrically focused beam where inconsistencies introduced by the quadrupoles have been compensated for by the octupole magnets producing a higher quality dose distribution in the target volume. The control system can dynamically adjust the parameters to optimize the beam determined by the treatment planning system. It is understood that the magnet configurations disclosed herein are merely exemplary, and that other combinations of magnets may be used to correct for other magnet-induced inconsistencies.

Certain embodiments may dynamically control beam depth by utilizing a posterior solenoidal magnet to produce a magnetic field gradient within the target volume such that the electrons reverse direction at a depth determined by the magnetic field strength. An anterior solenoidal magnet may be used in conjunction with the posterior magnet to modify the magnetic field in the target volume and enhance the dose deposition. The localized high dose region depth may be controlled with a control system designed to adjust the solenoid currents based on the desired dose distribution.

Exemplary embodiments include an apparatus for controlling a radiotherapy electron beam, where the apparatus comprises: an electron beam generator configured to generate an electron beam; a plurality of magnets producing a plurality of magnetic fields configured to focus the electron beam to a focal spot; and a control system configured to alter one or more parameters of the plurality of magnets to move the focal spot from a first location to a second location, where the first location is located at a first depth within a target region and the second location is located at a second depth within the target region.

In certain embodiments, the target region is below an epidermal surface of a subject; the first location or the second location is at a depth between 0 and 50 centimeters from the epidermal surface. In particular embodiments, the electron beam has a energy of between 50 and 250 megaelectron volts (MeV). In some embodiments, the energy of the beam is not modulated when the focal spot is moved from the first location to the second location. In specific embodiments, the plurality of magnets comprise a plurality of collinear multipole magnets. In certain embodiments, the plurality of collinear multipole magnets comprises at least two collinear quadrupole magnets.

In particular embodiments, the one or more parameters of the plurality of magnets comprises a separation distance between the plurality of collinear multipole magnets; and the control system is configured to alter the separation distance between the plurality of collinear multipole magnets. In some embodiments, the plurality of magnets comprise an anterior lens magnet, a posterior reflective magnet, and a plurality of radial focal magnets. In specific embodiments, the plurality of magnets comprise electromagnets; the one or more parameters of the plurality of magnets comprises an electrical current through the electromagnets; and the control system is configured to alter the electrical current through the electromagnets. In certain embodiments, the electromagnets are iron-dominated or coil dominated superconducting electromagnets.

In particular embodiments, the plurality of magnetic fields are configured to focus the electron beam at a convergence angle of between 50 and 500 mrad. In some embodiments, the plurality of magnetic fields are configured to focus the electron beam at a convergence angle of between 200 and 400 mrad. In specific embodiments, the control system comprises an algorithm to calculate the one or more parameters of the plurality of magnets. In certain embodiments, the control system receives input from a treatment planning software program configured to calculate a dose distribution. In particular embodiments, the focal spot comprises a maximum electron dose concentration.

Exemplary embodiments include a method of controlling a radiotherapy electron beam, where the method comprises: generating an electron beam; directing the electron beam through a plurality of magnetic fields produced by a plurality of magnets; focusing the electron beam to a focal spot with the plurality of magnetic fields; and altering one or more parameters of the plurality of magnets to move the focal spot from a first location to a second location where the first location is located at a first depth within a target region and the second location is located at a second depth within the target region.

In certain embodiments, the target region is below an epidermal surface of a subject; and the first location or the second location is at a depth between 0 and 50 centimeters from the epidermal surface. In particular embodiments, the electron beam has a power of between 50 megaelectron volts and 250 megaelectron volts. In some embodiments, the power of the beam is not modulated when the focal spot is moved from the first location to the second location. In specific embodiments, the plurality of magnets comprise a plurality of collinear multipole magnets. In certain embodiments, the plurality of collinear multipole magnets comprises at least three collinear quadrupole magnets.

In particular embodiments, the one or more parameters of the plurality of magnets comprises a separation distance between the plurality of collinear multipole magnets; and the control system is configured to alter the separation distance between the plurality of collinear multipole magnets. In some embodiments, the plurality of magnets comprise an anterior lens magnet, a posterior reflective magnet, and a plurality of radial focal magnets. In specific embodiments, the plurality of magnets comprise electromagnets; the one or more parameters of the plurality of magnets comprises an electrical current through the electromagnets; and the control system is configured to alter the electrical current through the electromagnets.

In certain embodiments, the plurality of magnetic fields are configured to focus the electron beam at a convergence angle of between 100 and 500 mrad. In particular embodiments, the plurality of magnetic fields are configured to focus the electron beam at a convergence angle of between 200 and 400 mrad. In some embodiments, the control system comprises an algorithm to calculate the one or more parameters of the plurality of magnets. In specific embodiments, the control system receives input from a treatment planning software program configured to calculate a dose distribution. In certain embodiments, the focal spot comprises a maximum electron dose concentration.

Exemplary embodiments include an apparatus for controlling a radiotherapy electron beam, where the apparatus comprises: an electron beam generator configured to generate an electron beam with a power between 50 megaelectron volts and 250 megaelectron volts; a plurality of magnets configured to focus the electron beam at a focal spot; and a control system configured move the focal spot from a first location at a first depth to a second location at a second depth, wherein the power of the electron beam is maintained at a consistent level when the focal spot is moved from the first location to the second location.

In certain embodiments, the first location and the second location are located within a target region. In particular embodiments, the target region is below an epidermal surface of a subject; and the first location or the second location is at a depth between 10 and 20 centimeters from the epidermal surface. In some embodiments, the control system is configured to alter one or more parameters of the plurality of magnets to move the focal spot from the first location to the second location. In specific embodiments, the control system comprises an algorithm to calculate the one or more parameters of the plurality of magnets.

In certain embodiments, the control system receives input from a treatment planning software program configured to calculate a dose distribution. In particular embodiments, the plurality of magnets comprise a plurality of collinear multipole magnets. In some embodiments, the plurality of collinear multipole magnets comprises at least three collinear quadrupole magnets. In specific embodiments, the one or more parameters of the plurality of magnets comprises a separation distance between the plurality of collinear multipole magnets; and the control system is configured to alter the separation distance between the plurality of collinear multipole magnets.

In certain embodiments, the plurality of magnets comprise an anterior lens magnet, a posterior reflective magnet, and a plurality of radial focal magnets. In particular embodiments, the plurality of magnets comprise electromagnets; the control system is configured to alter one or more parameters of the plurality of magnets to move the focal spot from the first location to the second location; the one or more parameters of the plurality of magnets comprises an electrical current through the electromagnets; and the control system is configured to alter the electrical current through the electromagnets.

In particular embodiments, the plurality of magnets are configured to focus the electron beam at a convergence angle of between 100 and 500 mrad. In some embodiments, the plurality of magnets are configured to focus the electron beam at a convergence angle of between 200 and 400 mrad. In specific embodiments, the focal spot comprises a maximum electron dose concentration.

Certain embodiments include a method of controlling a radiotherapy electron beam, where the method comprises: generating an electron beam having a power between 50 megaelectron volts and 250 megaelectron volts; focusing the electron beam to a focal spot with a plurality of magnets; and moving the focal spot from a first location at a first depth to a second location at a second depth while maintaining the power of the electron beam at a consistent level.

In particular embodiments, the first location and the second location are located within a target region. In certain embodiments, the target region is below an epidermal surface of a subject; the first location or the second location is at a depth between 10 and 20 centimeters from the epidermal surface. In some embodiments, moving the focal spot from a first location at a first depth to a second location at a second depth comprises altering one or more parameters of the plurality of magnets. In specific embodiments, the control system comprises an algorithm to calculate the one or more parameters of the plurality of magnets. In particular embodiments, the control system receives input from a treatment planning software program configured to calculate a dose distribution. In certain embodiments, the plurality of magnets comprise a plurality of collinear multipole magnets. In some embodiments, the plurality of collinear multipole magnets comprises at least three collinear quadrupole magnets.

In specific embodiments, the one or more parameters of the plurality of magnets comprises a separation distance between the plurality of collinear multipole magnets; and altering one or more parameters of the plurality of magnets comprises altering the separation distance between the plurality of collinear multipole magnets. In certain embodiments, the plurality of magnets comprise an anterior lens magnet, a posterior reflective magnet, and a plurality of radial focal magnets. In particular embodiments, the plurality of magnets comprise electromagnets; and moving the focal spot from a first location at a first depth to a second location at a second depth comprises altering an electrical current through the electromagnets.

In certain embodiments, the plurality of magnets are configured to focus the electron beam at a convergence angle of between 100 and 500 mrad. In particular embodiments, the plurality of magnets are configured to focus the electron beam at a convergence angle of between 200 and 400 mrad. In some embodiments, the focal spot comprises a maximum electron dose concentration.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The terms "about", "substantially" and "approximately" mean, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE FIGURES

The following drawings form part of the present specification and are included to further demonstrate certain aspects of the present invention. The present disclosure may be better understood by reference to one or more of these drawings in combination with the detailed description of specific embodiments presented herein.

DETAILED DESCRIPTION OF ILLUSTRATIVE EMBODIMENTS

Figure 1:
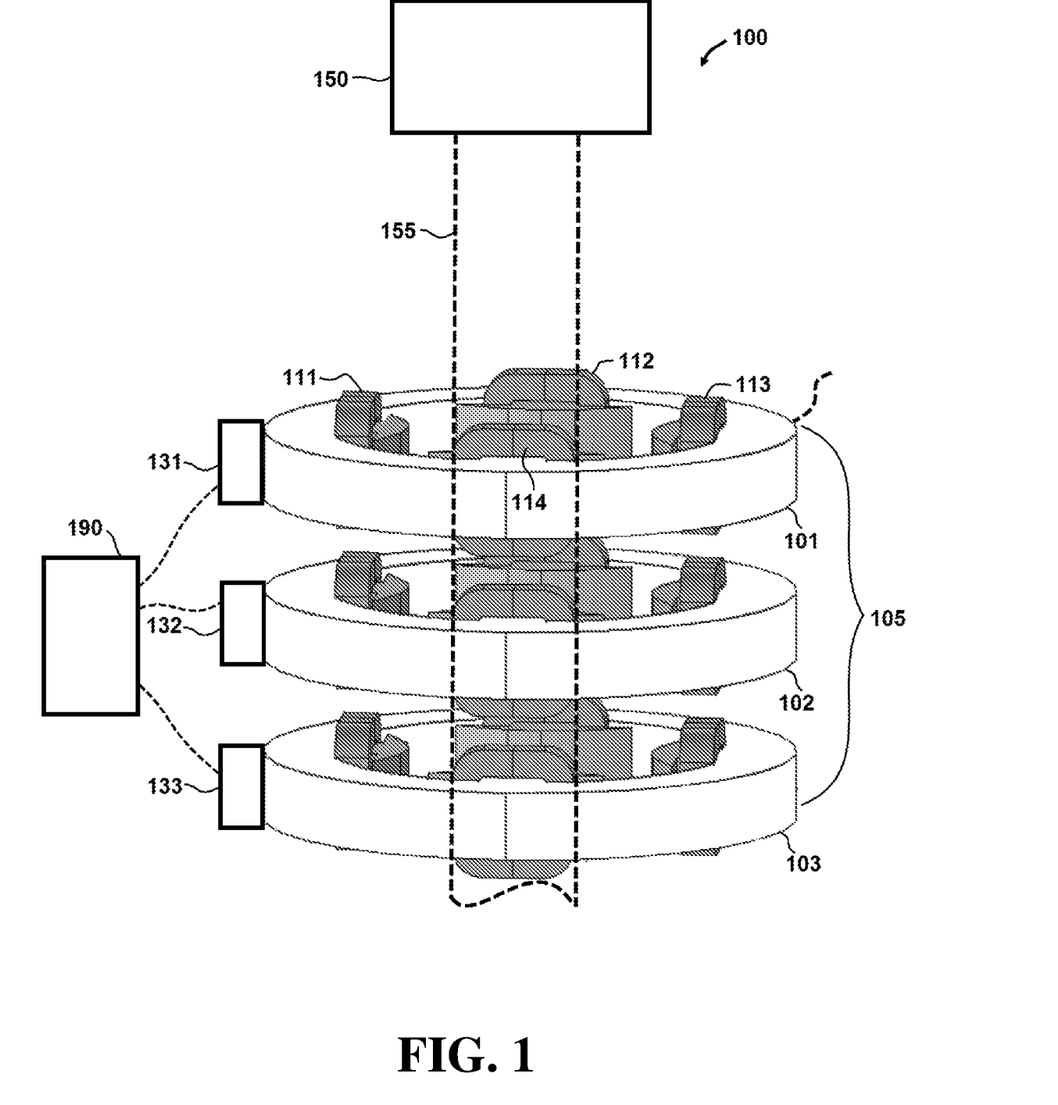
FIG. 1 displays a schematic of an apparatus for controlling a radiotherapy electron beam according to exemplary embodiments of the present disclosure.

Referring initially to FIG. 1, an apparatus 100 for controlling a radiotherapy electron beam is shown. In this embodiment, apparatus 100 comprises an electron beam generator 150 configured to generate an electron beam 155. Apparatus 100 further comprises a plurality of magnets 105 that includes collinear multipole magnets.

Figure 2:
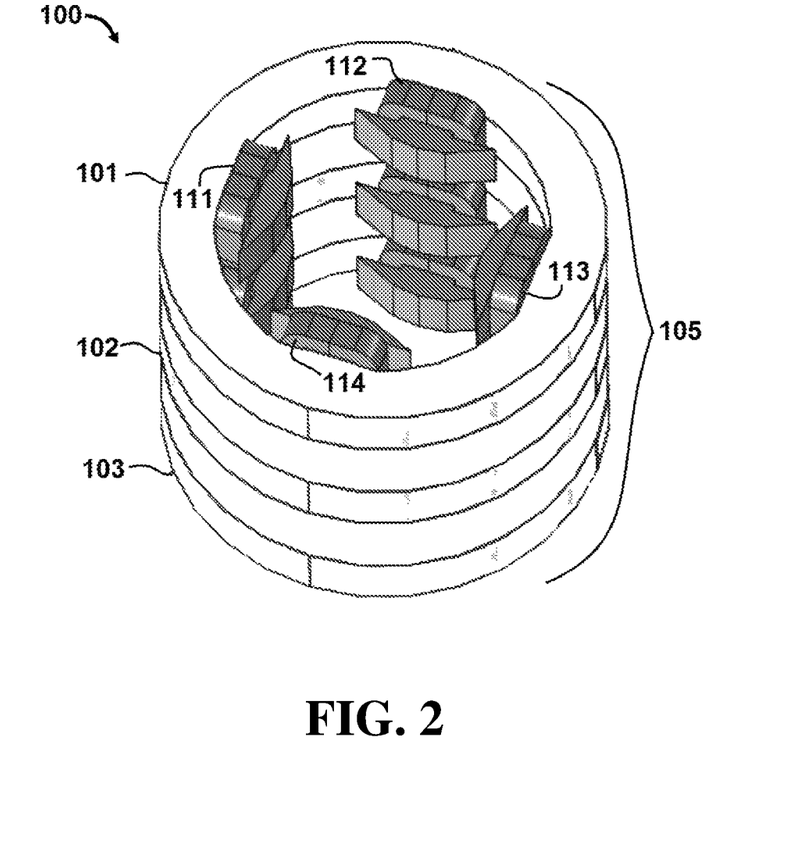
FIG. 2 displays a perspective view of an arrangement of magnets in the embodiment of FIG. 1

In this embodiment, magnets 105 include a first quadrupole magnet 101, a second quadrupole magnet 102 and a third quadrupole magnet 103. First quadrupole magnet 101 comprises first pole 111, second pole 112, third pole 113 and fourth pole 114. It is understood that second quadrupole magnet 102 and third quadrupole magnet 103 also comprise four poles (not labeled in the figures for purposes of clarity). A top perspective view of magnets 105 is shown in FIG. 2.

Figure 3:
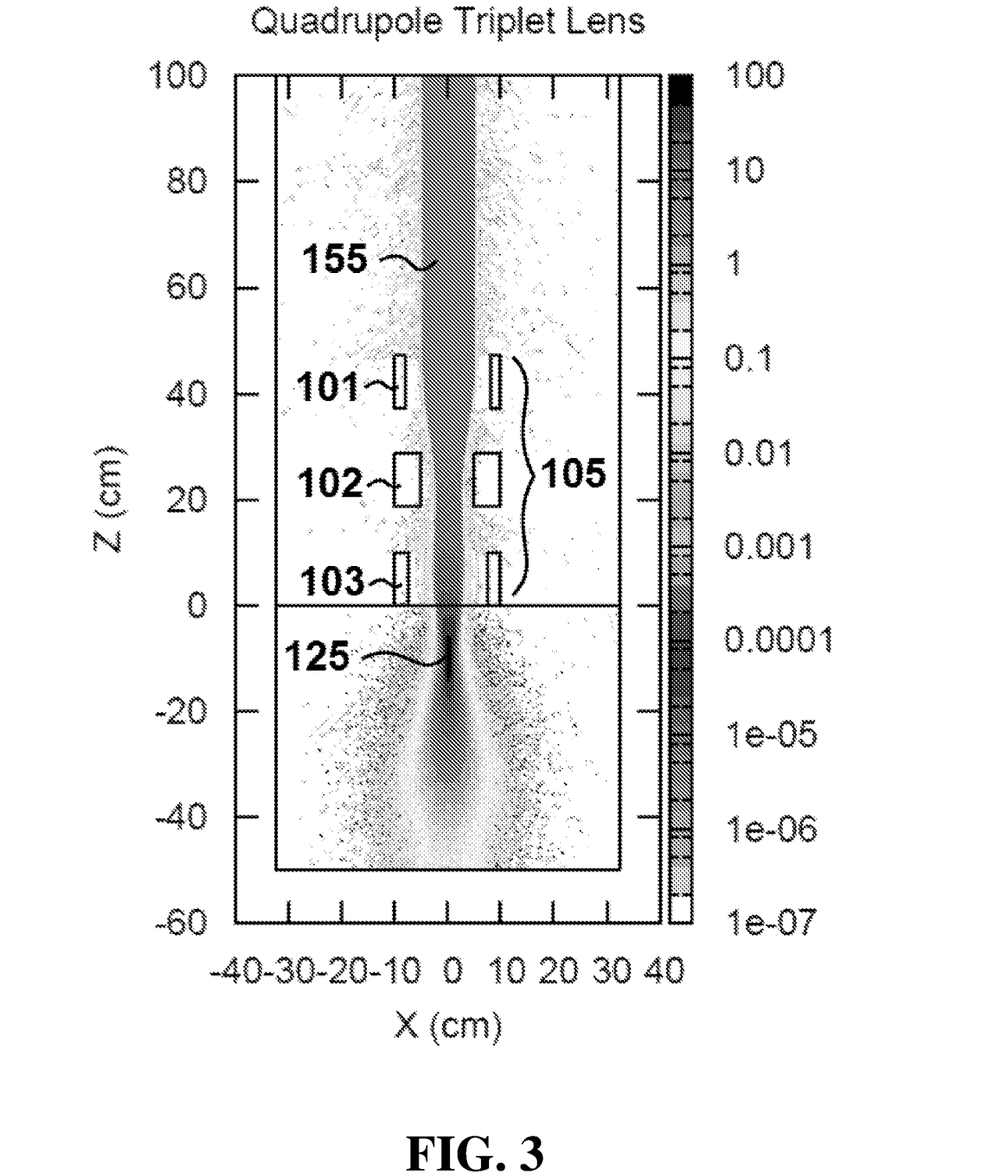
FIG. 3 displays a simulated dose distribution plot in the X-Z plane of the embodiment of FIG. 1.
Figure 4:
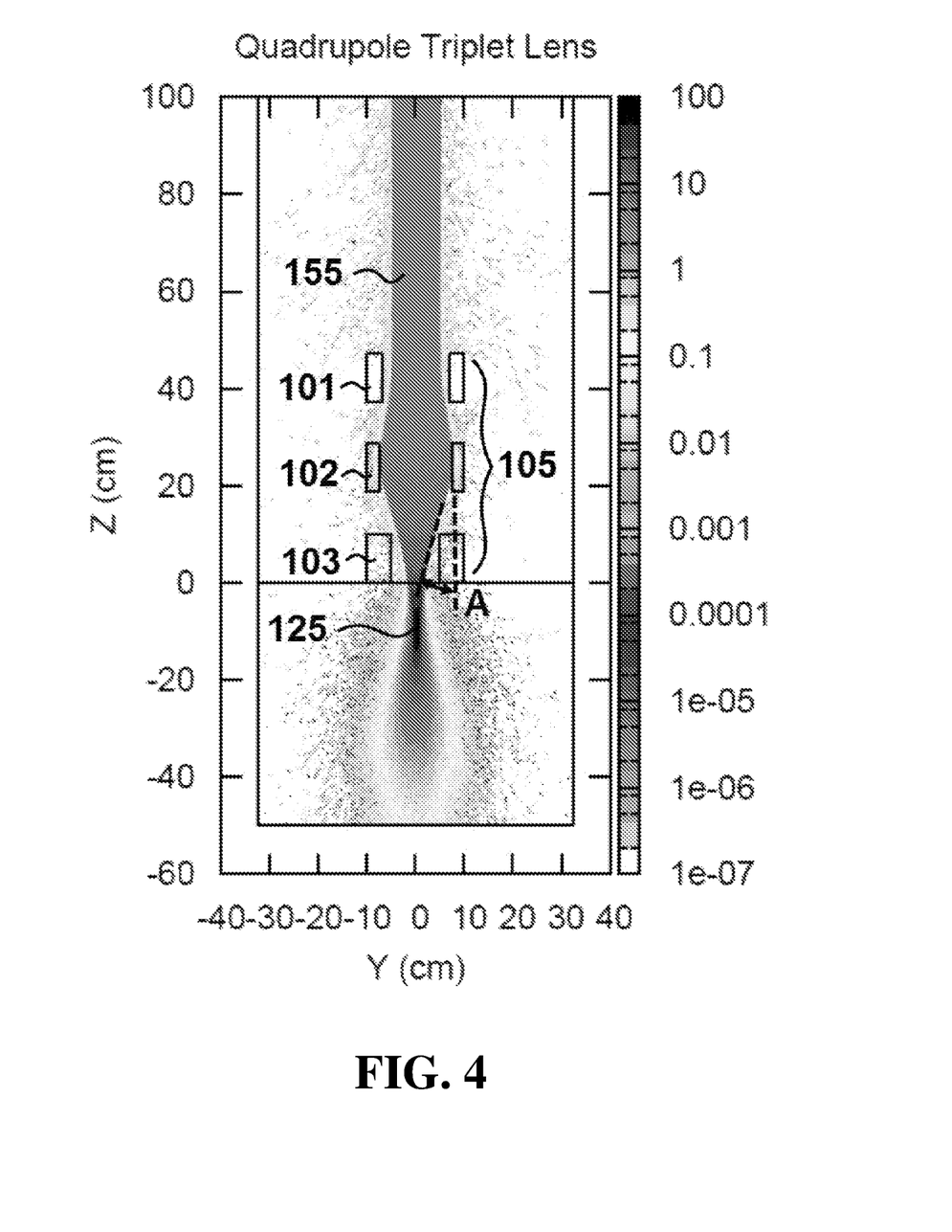
FIG. 4 displays a simulated dose distribution plot in the Y-Z plane of the embodiment of FIG. 1.

During operation of apparatus 100, magnets 105 produce a plurality of magnetic fields configured to focus electron beam 155 and provide a maximum electron dose concentration at a focal spot in a target region. Referring specifically to FIGS. 3 and 4, simulated dose distribution plots are shown for apparatus 100 in the X-Z plane (FIG. 3) and Y-Z plane (FIG. 4). Dose distributions where calculated using the Monte Carlo calculation code FLUKA© which is a general purpose code for simulating the interactions of energetic particles in matter. See "The FLUKA Code: Developments and Challenges for High Energy and Medical Applications" T. T. Böhlen, F. Cerutti, M. P. W. Chin, A. Fassò, A. Ferrari, P. G. Ortega, A. Mairani, P. R. Sala, G. Smirnov and V. Vlachoudis, Nuclear Data Sheets 120, 211-214 (2014); see also "FLUKA: a multi-particle transport code" A. Ferrari, P. R. Sala, A. Fassò, and J. Ranft, CERN-2005-10 (2005), INFN/TC_05/11, SLAC-R-773. FIGS. 3 and 4 were produced by tracking $2.5 \times 10^5$ with a minimum step size of 0.05 cm, charged particle cutoff energy of 10 keV, and dose binning grid size of 1 mm. In this example, electron beam 155 is a 100 megaelectron volt (MeV), 5 centimeter radius electron beam. Electron beam 155 is shown passing through 100 centimeters of air and incident on a water phantom (at Z dimension 0 centimeters, corresponding to an epidermal surface of a subject). In the illustrated embodiment, magnets 105 are configured as a quadrupole triplet and function as a symmetric uniform focusing lens.

As shown in FIG. 3, first quadrupole magnet 101 focuses electron beam 155 in the X-Z plane, while second quadrupole magnet 102 defocuses electron beam 155, and third quadrupole magnet 103 focuses electron beam 155. As shown in FIG. 4, magnets 101, 102 and 103 perform the inverse operations on electron beam 155 in the Y-Z plane. In particular, first quadrupole magnet 101 defocuses beam 155 in the Y-Z plane, while second quadrupole magnet 102 focuses electron beam 155, and third quadrupole magnet 103 defocuses electron beam 155.

As shown in FIGS. 3 and 4, magnets 105 may be configured to focus electron beam 155 and provide a maximum electron dose concentration at a focal point 125. As explained further below, during operation control system 190 (shown in FIG. 1) can alter one or more parameters of magnets 105 to move focal spot 125 to different depths within a target region in the Z-plane. In exemplary embodiments, the power of electron beam 155 is not modulated when focal spot 125 is moved to different depths within a target region.

For example, control system 190 may control the position of individual magnets in the group of magnets 105 in order to alter the separation distance between the magnets. In particular, control system 190 may alter the separation distance between first quadrupole magnet 101 and second quadrupole magnet 102. Control system 190 may also alter the separation distance between second quadrupole magnet 102 and third quadrupole magnet 103.

The separation distance between magnets 101, 102 and 103 may be altered by any one of suitable mechanisms, including for example, one or more linear actuators. For example, as shown in FIG. 1, control system 190 can control the position of magnets 101, 102 and 103 via linear actuators 131, 132 and 133 respectively. By adjusting the position of each magnet 101, 102 and 103, the separation distances between the magnets can be altered. The alteration of the separation distances between magnets in the group of magnets 105 affects the focusing of electron beam 155 and convergence angle A, shown in FIG. 4.

As convergence angle A is increased, focal spot 125 is moved closer to magnets 105. Conversely, as the separation distance between magnets 105 is controlled to decrease convergence angle A, focal spot 125 is moved farther from magnets 105. In certain embodiments, apparatus 100 can increase convergence angle A up to values of approximately 400 milliradians. This can allow focal spot 125 to be moved within the target region, which is typically between 0 and 35 centimeters from the surface. It is understood that a similar convergence angle is present in the X-Z plane of FIG. 3. The convergence angle present in FIG. 3 is not labeled for purposes of clarity.

In other embodiments, control system 190 may control different parameters in order to control electron beam 155 and focal spot 125. For example, in certain embodiments magnets 105 may comprise electromagnets and control system 190 can be configured to alter the electrical current through the electromagnets. Similar to the magnet separation distance, altering the electrical current through each of magnets 101, 102 and 103 can also affect convergence angle A and the position of focal spot 125. Accordingly, the alteration of magnet parameters (e.g. magnet separation distance or electrical current) can change the depth of focal spot 125 by allowing focal spot 125 to be moved closer to and farther from magnets 105 in an axial direction (e.g. collinear with electron beam 155).

The ability to control convergence angle A and the location of focal spot 125 via magnetic parameters can provide numerous advantages. For example, the radiation dose can be reduced in regions outside of the target region. In particular, the ability to create a higher convergence angle can provide a larger cross section of beam 155 at the skin surface as compared to the cross section at focal spot 125. Particular embodiments may be capable of producing surface entrance doses as low as fifteen percent of the maximum dose at the focal spot 125, as opposed to typical current technologies that provide surface doses of approximately eighty or ninety percent of the maximum dosage. The ability to control the axial depth location of the focal spot and minimize radiation dosage levels to healthy tissues outside the target region can improve patient outcomes and reduce recovery times.

Furthermore, exemplary embodiments also provide the ability to control the depth of the radiation dose peak at focal point 125 within a target region without modulating the energy of beam 155. Current electron therapy technology typically varies the energy of the electron beam to adjust the depth of penetration, which is done manually and is not suited for dynamic control of the dosage level. For example, changing the energy of the beam to adjust the depth of penetration does not allow for independent control of focal spot depth and radiation levels.

In contrast, exemplary embodiments of the present disclosure are configured to penetrate the full clinical range of patient thicknesses and then use the magnetic system parameters to produce a high dose focal region in the target which may be moved throughout the target depth. The target depth can be controlled by parameters (e.g. magnet current and/or positions) other than electron beam energy levels.

As a result of dose peak depth control as disclosed herein, beams of varying dose peak depths may be superimposed to produce a region of constant dose over a region of depth within the patient corresponding to a tumor or treatment site.

Figure 5:
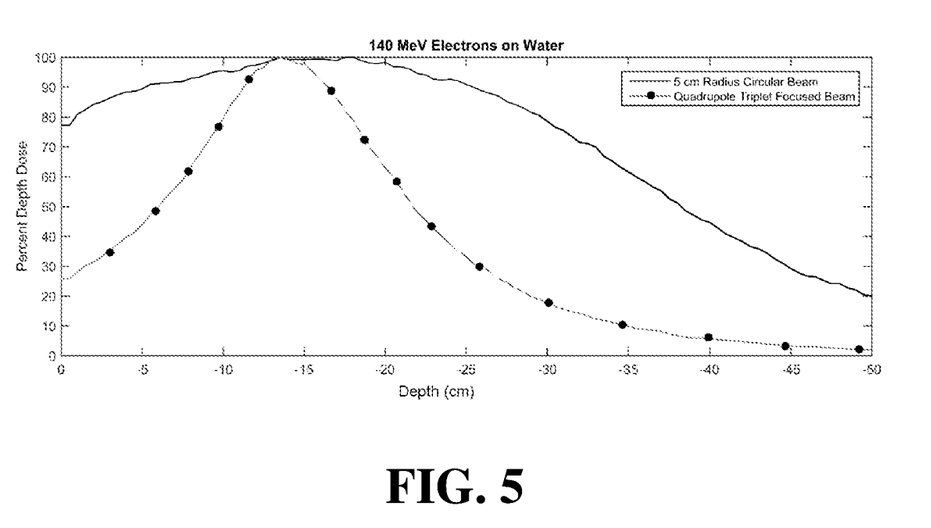
FIG. 5 displays a graph of a simulated percent dose distribution curves for the embodiment of FIG. 1 compared to an unfocused electron beam.

FIG. 5 illustrates a graph of a simulated percent dose distributions for 140 MeV electron beams on water for a 5 centimeter radius circular beam. In one plot of FIG. 5, the electron beam is not focused, while in the other plot the same beam is focused with a collinear quadrupole magnet configuration as shown in FIGS. 1 and 2. As shown in FIG. 5, the percent dose at the surface (e.g. depth of 0 cm) is substantially reduced for the focused beam as compared to the unfocused beam. The focused beam provides a dose at the surface of between 20 and 30 percent of the maximum dose, while the unfocused beam provides a surface dose of between 70 and 80 percent of the maximum. FIG. 5 also illustrates the focused beam provided a maximum dose at slightly less than 15 cm depth.

Other embodiments may comprise a different configuration of magnets than those previously shown and described. For example, referring now to FIG. 6, an apparatus 200 comprises a plurality of magnets 205 that are not collinear and are configured to control an electron beam 255. In this embodiment, magnets 205 are configured as solenoidal electromagnets and comprise an anterior lens magnet 201, a posterior reflective magnet 202, and a plurality of radial focal magnets 203, 204, 206 and 207.

During operation of apparatus 200, a control system 290 can control parameters of magnets 205 to focus beam 255 at different depths, in a manner similar to the previously-described embodiments. For example, control system 290 can control an electrical current through each of magnets 201-204 and 206-207. Control system may also be configured to control the position of magnets 201-204 and 206-207 so that the separation distance between each of the magnets is altered to change the focal spot (not shown in FIG. 6 for purposes of clarity) of beam 255.

Figure 6:
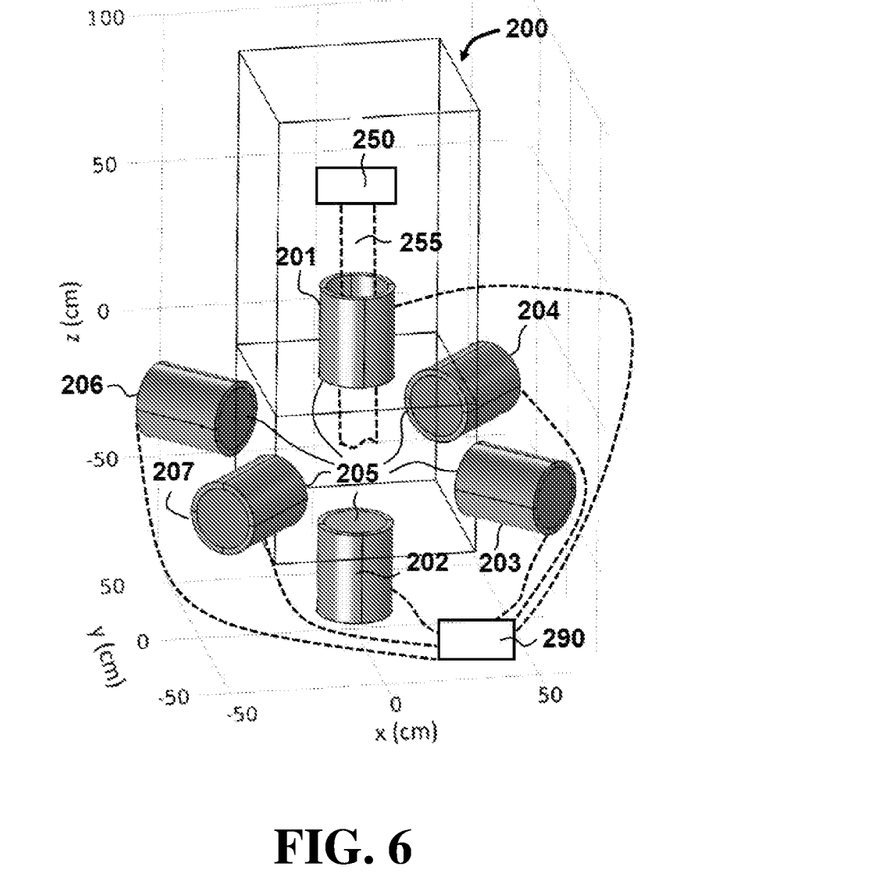
FIG. 6 displays a schematic of an apparatus for controlling a radiotherapy electron beam according to exemplary embodiments of the present disclosure.

In the configuration shown in FIG. 6, anterior lens magnet 201 is the primary source of focusing. Radial focal magnets 203, 204, 206 and 207 produce a magnetic field within the target that modifies the anterior lens magnet 201 field and provides additional focusing. The plane of radial focal magnets 203, 204, 206 and 207 can be adjusted based on the treatment depth. Posterior reflective magnet 202 produces a magnetic field gradient such that electrons are reflected at a depth dependent on the magnetic field strength of magnet 202, resulting in a radiation dose confined to a desired depth.

Figure 7:
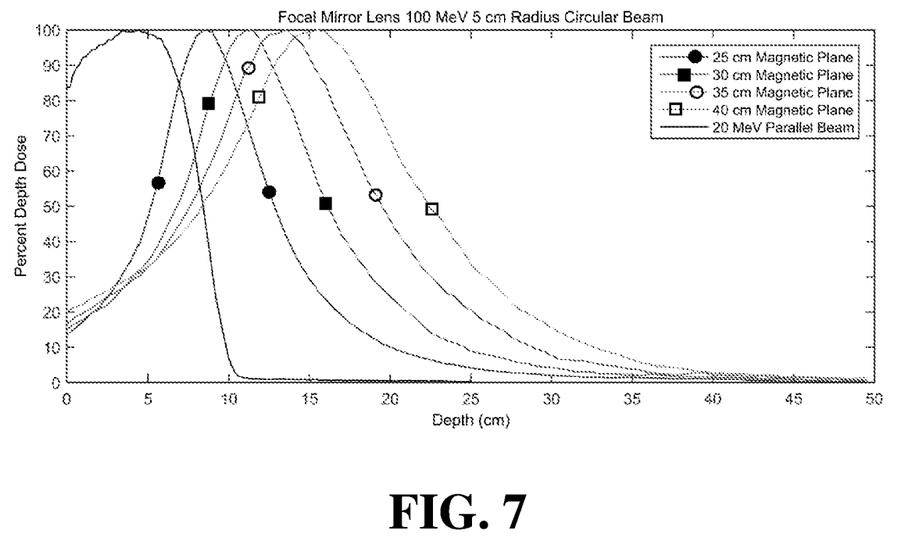
FIG. 7 illustrates a graph of simulated percent depth dose curves for different configurations of the embodiment of FIG. 1.

FIG. 7 illustrates a graph of simulated percent depth dose curves for 100 MeV, 5 cm radius electron beams incident on a water phantom, where the beam has been focused using the FIG. 6 configuration with different depths of the magnetic plane as defined by the in-plane magnets 203, 204, 206, and 207. As shown in FIG. 7, the different depths magnetic planes corresponds to a shift in the dose peak to different depths. The 40 cm magnetic plane has a maximum dose peak at approximately 16 cm, the 35 cm magnetic plane has a maximum dose peak at approximately 13.5 cm, the 30 cm magnetic plane has a maximum dose peak at approximately 11.5 cm, and the 25 cm magnetic plane has a maximum dose peak at approximately 8.5 cm. For comparison, the percent depth dose curve for a 5 cm radius circular beam of 20 MeV electrons without any focusing magnetic fields is shown. As shown in FIG. 7, the surface dose of the unfocused 20 MeV beam is between 80 and 90 percent, while the focused beams have a surface dose between 10 and 20 percent.

Figure 8:
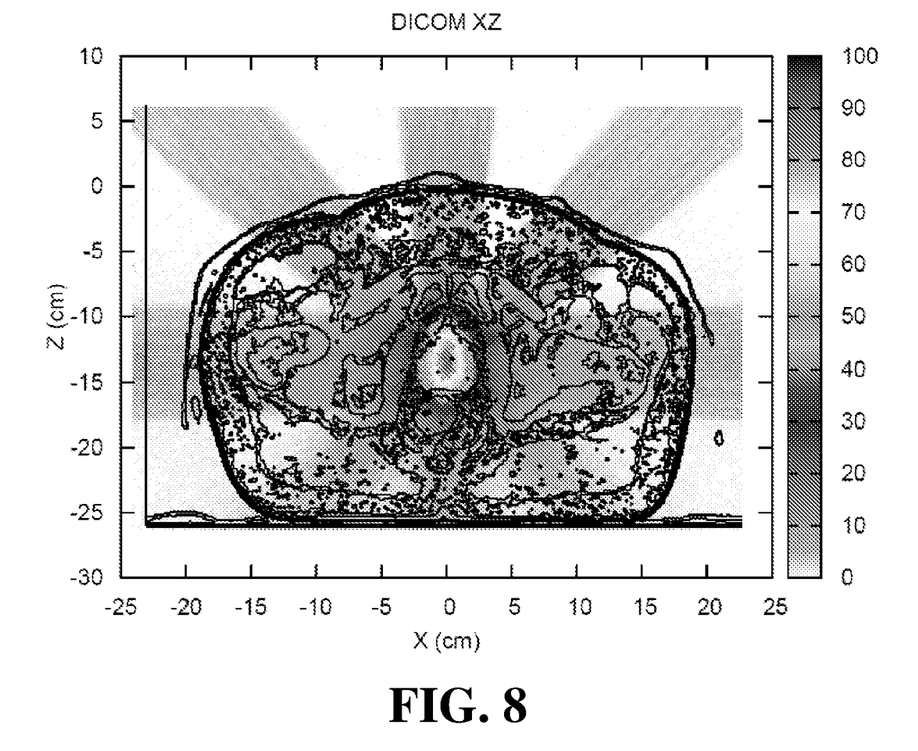
FIG. 8 illustrates a Monte Carlo calculation of a composite dose distribution from multiple electron beams focused on a prostate CT (computed tomography) image for the embodiment of FIG. 6.
Figure 9:
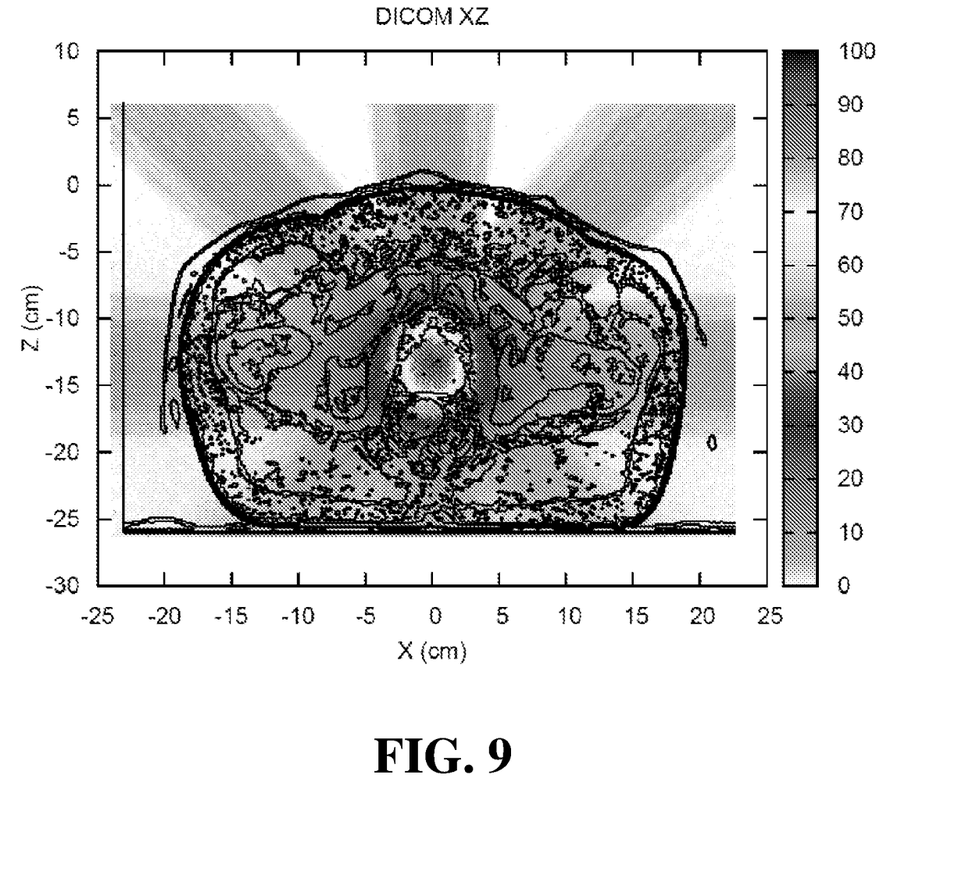
FIG. 9 illustrates a Monte Carlo calculation of a composite dose distribution from multiple electron beams focused on a prostate CT (computed tomography) image for the embodiment of FIG. 6.

FIG. 8 illustrates a Monte Carlo calculation of a composite dose distribution from five focused electron beams of varying energies on a prostate CT (computed tomography) image using the magnet configuration shown in FIG. 6. FIG. 9 illustrates a Monte Carlo calculation of a composite dose distribution from 10 focused electron beams of varying energies utilizing a form of "dose painting" (e.g. altering the depth of a focal spot for each of the beams). This technique can be been used to increase the high dose coverage throughout the prostate using the magnet configuration shown in FIG. 6.

Figure 10:
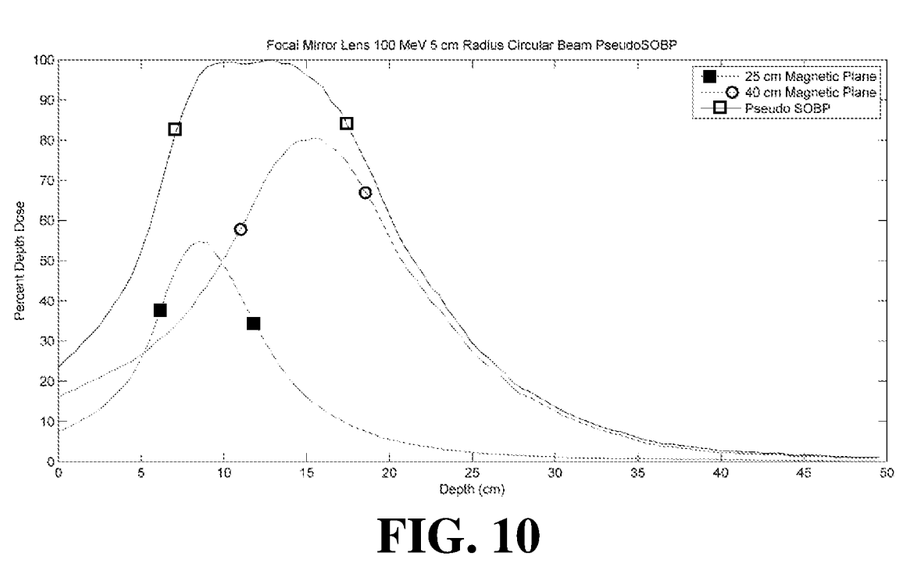
FIG. 10 illustrates a graph of simulated percent depth dose curves for different configurations of the embodiment of FIG. 6.

FIG. 10 illustrates a graph of the percent dose versus depth for different configurations of the embodiment shown in FIG. 6 utilizing radial focal magnets with an anterior lens magnet and a posterior reflective magnet. The graphs include a 25 centimeter magnetic plane configuration, a 40 centimeter magnetic plane configuration with the intensities of each distribution optimized to produce a simulated spread out Bragg peak ("pseudo SOBP") configuration. The graphs illustrated in FIG. 10 included simulated data for a 100 MeV electron beam with a 5 centimeter radius.

All of the devices, apparatus, systems and/or methods disclosed and claimed herein can be made and executed without undue experimentation in light of the present disclosure. While the devices, apparatus, systems and methods of this invention have been described in terms of particular embodiments, it will be apparent to those of skill in the art that variations may be applied to the devices, apparatus, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:
U.S. Pat. No. 4,806,766
U.S. Pat. No. 5,113,162
U.S. Pat. No. 5,161,546
U.S. Pat. No. 6,292,538
U.S. Pat. No. 8,436,326
U.S. Pat. No. 8,350,226
U.S. Pat. No. 8,933,651
U.S. Pat. No. 9,095,705
U.S. Pat. No. 9,153,409
U.S. Pat. No. 9,283,407
U.S. Pat. No. 9,289,624
U.S. Pat. Pub. 2011/0180731
U.S. Pat. Pub. 2015/0187538
PCT Pat. Pub. WO2015/102680
PCT Pat. Pub. WO2012/070054
Korean Pat. Pub. 101416559B1

"An Adjustable, Short-Focal Length Permanent-Magnet Quadrupole Based Electron Beam Final Focus System", Kim et al., Mar. 11, 2005 available at http://pbpl.physics.ucla.edu/Research/Experiments/Beam_Radiation_Interaction/Thomson_Scattering/_references/PMQ_final_print.pdf "Laser-Driven Very High Energy Electron/Photon Beam Radiation Therapy in Conjunction with a Robotic System", Nakajima et al., Appl. Sci. 2015, 5, 1-20.

"The FLUKA Code: Developments and Challenges for High Energy and Medical Applications" T. T. Böhlen, F. Cerutti, M. P. W. Chin, A. Fassò, A. Ferrari, P. G. Ortega, A. Mairani, P. R. Sala, G. Smirnov and V. Vlachoudis, Nuclear Data Sheets 120, 211-214 (2014).

"FLUKA: a multi-particle transport code" A. Ferrari, P. R. Sala, A. Fassò, and J. Ranft, CERN-2005-10 (2005), INFN/TC_05/11, SLAC-R-773.

The invention claimed is:

1. An apparatus for controlling a radiotherapy electron beam, the apparatus comprising:
    an electron beam generator configured to generate an electron beam;
    a plurality of magnets producing a plurality of magnetic fields configured to focus the electron beam to a focal spot; and
    a control system configured to alter one or more parameters of the plurality of magnets to move the focal spot from a first location to a second location, wherein the first location is located at a first depth within a target region and the second location is located at a second depth within the target region.

2. The apparatus of claim 1 wherein:
    the target region is below an epidermal surface of a subject; and
    the first location or the second location is at a depth between 0 and 50 centimeters from the epidermal surface.

3. The apparatus of claim 1 wherein the electron beam has a energy of between 50 and 250 megaelectron volts (MeV).

4. The apparatus of claim 3 wherein the energy of the beam is not modulated when the focal spot is moved from the first location to the second location.

5. The apparatus of claim 1 wherein the plurality of magnets comprise a plurality of collinear multipole magnets.

6. The apparatus of claim 5 wherein the plurality of collinear multipole magnets comprises at least two collinear quadrupole magnets.

7. The apparatus of claim 5 wherein:
    the one or more parameters of the plurality of magnets comprises a separation distance between the plurality of collinear multipole magnets; and
    the control system is configured to alter the separation distance between the plurality of collinear multipole magnets.

8. The apparatus of claim 1 wherein the plurality of magnets comprise an anterior lens magnet, a posterior reflective magnet, and a plurality of radial focal magnets.

9. The apparatus of claim 1 wherein:
    the plurality of magnets comprise electromagnets;
    the one or more parameters of the plurality of magnets comprises an electrical current through the electromagnets; and
    the control system is configured to alter the electrical current through the electromagnets.

10. The apparatus of claim 9 wherein the electromagnets are iron-dominated or coil dominated superconducting electromagnets.

11. The apparatus of claim 1 wherein the plurality of magnetic fields are configured to focus the electron beam at a convergence angle of between 50 and 500 mrad.

12. The apparatus of claim 1 wherein the plurality of magnetic fields are configured to focus the electron beam at a convergence angle of between 200 and 400 mrad.

13. The apparatus of claim 1 wherein the control system comprises an algorithm to calculate the one or more parameters of the plurality of magnets.

14. The apparatus of claim 13 wherein the control system receives input from a treatment planning software program configured to calculate a dose distribution.

15. The apparatus of claim 1 wherein the focal spot comprises a maximum electron dose concentration.

16. A method of controlling a radiotherapy electron beam, the method comprising:
generating an electron beam;
directing the electron beam through a plurality of magnetic fields produced by a plurality of magnets;
focusing the electron beam to a focal spot with the plurality of magnetic fields; and
altering one or more parameters of the plurality of magnets to move the focal spot from a first location to a second location wherein the first location is located at a first depth within a target region and the second location is located at a second depth within the target region.

17. An apparatus for controlling a radiotherapy electron beam, the apparatus comprising:
an electron beam generator configured to generate an electron beam with a power between 50 megaelectron volts and 250 megaelectron volts;
a plurality of magnets configured to focus the electron beam at a focal spot; and
a control system configured move the focal spot from a first location at a first depth to a second location at a second depth, wherein the power of the electron beam is maintained at a consistent level when the focal spot is moved from the first location to the second location.

18. The apparatus of claim 17 wherein the control system is configured to alter one or more parameters of the plurality of magnets to move the focal spot from the first location to the second location.

19. The apparatus of claim 18 wherein the control system comprises an algorithm to calculate the one or more parameters of the plurality of magnets.

20. A method of controlling a radiotherapy electron beam, the method comprising:
generating an electron beam having a power between 50 megaelectron volts and 250 megaelectron volts;
focusing the electron beam to a focal spot with a plurality of magnets; and
moving the focal spot from a first location at a first depth to a second location at a second depth while maintaining the power of the electron beam at a consistent level.

* * * * *